United States Patent [19]

Kovach

[11] Patent Number: 5,314,815
[45] Date of Patent: May 24, 1994

[54] METHOD FOR TEMPORARILY INHIBITING OR DEACTIVATING SERINE HYDROLASE AND ADDUCT OF SERINE HYDROLASE WITH A PHOSPHONATE OR PHOSPHATE COMPOUND

[75] Inventor: Ildiko M. Kovach, Montgomery County, Md.

[73] Assignee: The Catholic University of America, Washington, D.C.

[21] Appl. No.: 850,112

[22] Filed: Mar. 4, 1992

[51] Int. Cl.$^5$ .................. C12N 9/99; C12N 9/100; C12N 9/96
[52] U.S. Cl. ............................ 435/184; 435/188; 435/183; 435/219
[58] Field of Search .............. 435/188, 184, 183, 219

[56] References Cited

FOREIGN PATENT DOCUMENTS 3-160086  7/1991  Japan .

OTHER PUBLICATIONS

Kabanova et al., "*Complex Lipids,* Synthesis of 1-O-Palmitoyl-2-O . . . " Zh. Obshch. Khim., 43(1), 193-9, 1973.
Kopelevich et al., "Acyl group carriers VIII. Synthesis of 4'-O-. . . ", Khim. Prir. Soedin., 5(3), 174-6, 1969.
Brandt et al., Biochemical Pharmacology, vol. 29, pp. 1927-1931, 1980, "Selective Inhibition of Rat Liver . . . ".
Pavanaram et al., Experientia, vol. 28, No. 5, pp. 497-9, 1972, "Phosphatidyl-N-(2-Hydroxyethyl)-. . . ".
Lieske et al., "Participation of a Neighbouring Oxime Group . . . ", Chemical Communications, (1), 13-14, 1968.
Ramirez et al., J. of Organic Chemistry, vol. 42, No. 5, pp. 771-778, 1977.
Martin et al., Tetrahedron Letters, vol. 29, No. 30, pp. 3631-3634, 1988.
Kuyl-Yeheskiely et al., Tetrahedron, vol. 44, No. 20, pp. 6515-6523, 1988.
Kuyl-Yeheskiely et al., Nucleic Acids Research, vol. 17, No. 8, pp. 2897-2905, 1989.
Carayon-Gentil et al., Bull. Soc. Chim. Fr., 5, 1616-20, 1967.

*Primary Examiner*—David M. Naff
*Assistant Examiner*—Michael V. Meller
*Attorney, Agent, or Firm*—Boris Haskell

[57] ABSTRACT

Phenacyl phosphonate adducts of serine hydrolases temporarily inhibit or inactivate the serine hydrolases. The serine hydrolases are activated by intramolecularly catalyzed dephosphonylation of the adduct over a period of time. Half-lives for dephosphonylation in the range of about 30 to 500 minutes have been observed at physiological pH's.

14 Claims, 2 Drawing Sheets

METHOD FOR TEMPORARILY INHIBITING OR DEACTIVATING SERINE HYDROLASE AND ADDUCT OF SERINE HYDROLASE WITH A PHOSPHONATE OR PHOSPHATE COMPOUND

SUMMARY OF THE INVENTION

The present invention relates to adducts of serine hydrolase enzymes with phosphonate esters. More particularly, the invention provides for the inhibition or inactivation of such enzymes by phosphonylation, and the subsequent intramolecularly catalyzed dephosphonylation of the adduct to reactivate the enzyme. Thus, the invention embraces the concept of control of enzyme activity by temporary deactivation, and the concept of "proenzyme", wherein the enzymes are held in an inactive state to be released into active state over a period of time.

The fact that phosphonate esters react with and are effective inhibitors of serine hydrolase enzymes is well recognized. However, such reactions as are known in the prior art are essentially irreversible and toxic. Pesticides and nerve gases are in this category. In accordance with the present invention, it has been discovered that certain phosphonate esters react with and inhibit the serine proteases reversibly. The half-life for dephosphonylation and full recovery of enzyme activity is pH dependent and is about 30 to 500 minutes at a physiological pH. The phosphonate esters of the present invention are exemplified by the phenyl phenacyl phosphonates. Specific preferred examples of these compounds are: 4-nitrophenyl phenacyl methylphosphonate (PMN), 4-nitrophenyl 4-nitrophenacyl methylphosphonate (NPMN), 4-nitrophenyl 4-methylphenacyl methylphosphonate (MPMN), 4-nitrophenyl 4-methoxyphenacyl methylphosphonate (MOPMN), and 4-nitrophenyl 4-chlorophenacyl methylphosphonate (CPMN). These phosphonate esters are particularly useful as reversible inhibitors for such enzymes as acetylcholinesterases; chymotrypsin, and similar enzymes such as mast cell chymase and cathepsin G; trypsin and similar enzymes, thrombin, plasmin, and tissue-type plasminogen activator enzyme (t-PA); phospholipases; serine proteases in tumor proliferation and sperm production. These are enzymes of great medical interest, since their uncontrolled activity is the origin of certain disease states, some of which are Alzheimer's disease, myastenia gravis, glaucoma, pancreatitis, inflammation and rheumatoid arthritis, blood-diseases, hemophilias, cardiovascular diseases, thrombus, emphysema and carcinomas. Moreover, proteolysis by serine proteases is a major problem in protein engineering and operations related to protein purifications and storage. The aforesaid phosphonate esters can be synthesized according to the procedures described by C. N. Lieske et al., *Agricultural and Food Chemistry*, Vol. 17, 256 (1969).

As illustrative of the invention, PMN was found to inactivate rapidly and effectively chymotrypsin, trypsin, thrombin, tissue-type plasminogen activator enyme (t-PA), and plasmin, and the enzymes are fully reactivated in one to ten hours at 25° C., at a physiological pH.

The phenyl phenacyl phosphonates are only illustrative of the invention, and other related phosphonate or phosphate compounds are contemplated. These may be represented by the following general formula

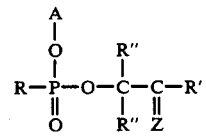

wherein: R is an alkyl or alkoxy radical, and preferably a lower alkyl radical such as one having one to four carbon atoms, and is preferably methyl; A is an aromatic radical such as a phenyl or a naphthyl radical, and is preferably a para substituted phenylene, such as nitro, chloro, methoxy or amino phenylene; R' is a phenyl or a lower alkyl radical, such as one having one to four carbon atoms, and is preferably phenyl; R" is hydrogen or methyl; and Z is an electronegative group such as oxygen, nitrogen or sulfur, or in place thereof a monovalent hydroxy or amino group and the extra carbon valence may be satisfied with a hydrogen atom.

It is accordingly one object of the present invention to provide for the reversible inactivation of serine hydrolase enzymes.

Another object of the present invention is to provide for the control of the activity of serine hydrolase enzymes by causing their reversible inactivation by means of a phosphonate adduct, with intramolecularly catalyzed dephosphonylation over a period of time.

Still another object of the present invention is to provide a proenzyme that is an adduct of a phosphonate ester and a serine hydrolase enzyme which is intramolecularly dephosphonylated over a period of time.

And still another object of the invention is to provide phosphonyl adducts of serine hydrolase enzymes that are intramolecularly dephosphonylated over a period of time.

Other objects and advantages of the present invention will become apparent to those skilled in the art, from a consideration of the following detailed description of the invention and certain specific embodiments thereof.

DESCRIPTION OF THE DRAWINGS

The following detailed description is had in conjunction with the accompanying drawings, wherein.

DETAILED DESCRIPTION OF THE INVENTION

Figure 1:
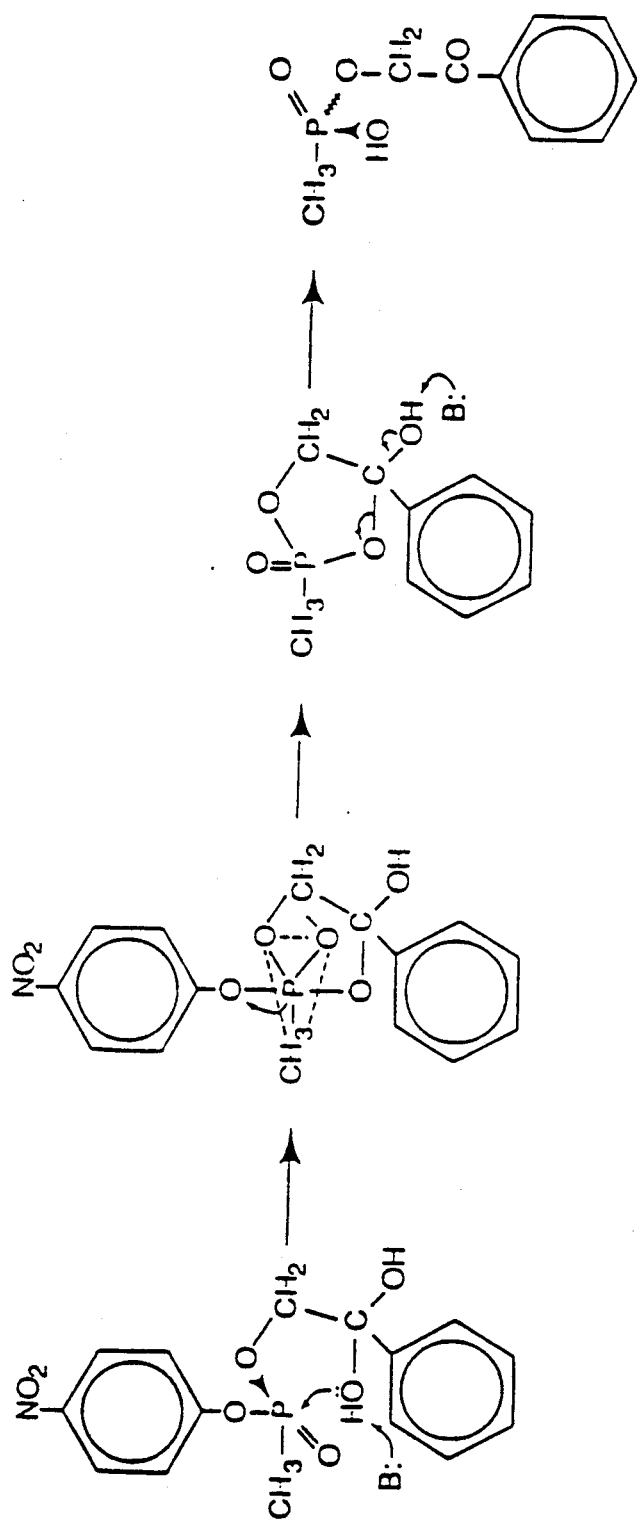
FIG. 1 illustrates the hydrolytic decomposition of 4-nitrophenyl phenacyl methyl phosphonate.

As stated above, the preferred phosphonate esters employed in the practice of the present invention are nitrophenyl phenacyl phosphonates. The synthesis of several such phosphonates is described.

Synthesis of 4-nitrophenyl phenacyl methylphosphonate (PMN) and 4-nitrophenyl 4-nitrophenacyl methylphosphonate (NPMN)

The synthesis of these compound was carried out according to C. N. Lieske et al., *Agricultural and Food Chemistry* Vol. 17, 256 (1969). PMN was obtained in 0.8 g. quantity and NPMN in 0.2 g. quantity. Analytical purity is 98% for PMN and 97% for NPMN based on basic hydrolysis to 4-nitrophenol (400 nm). The melting points are: PMN 112°–114° C. and NPMN 146°–47° C. Other properties also agreed with the earlier report.

Synthesis of 4-nitrophenyl 4-methoxyphenacyl methylphosphonate (MOPMN)

Bis 4-nitrophenyl methylphosphonate (NMN) and 4-nitrophenyl methylphosphonochloridate were made by coupling methyldichlorophosphonate with one equivalent of the Na salt of 4-nitrophenol in dry benzene. The NaCl and bis-4-nitrophenyl methylphosphonate precipitated out of benzene and were filtered out. The 4-nitrophenyl methylphosphonochloridate was then coupled with 2-hydroxy-4'-methoxyacetophenone in benzene in the presence of dry pyridine. The pyridine hydrochloride was filtered out of the benzene solution, and benzene was then evaporated and MOPMN was recrystallized from methanol acetone. Analytical purity is 97% based on hydrolysis to 4-nitrophenol. Melting point 112°–113° C. Other properties are in agreement with the above-cited report (C. N. Lieske et al.)

Synthesis of 2-hydroxy-4'methoxyacetophenone

It is used in the synthesis of MOPMN, above, and was synthesized from 2-bromo-4'-methoxyacetophenone (Aldrich). The 2-bromo-4'-methoxyacetophenone was refluxed in 20% water and N-methyl-2-pyrrolidinone for 10 hours at 105° C. The product was extracted with ethylether, dried over $MgSO_4$, the ether evaporated and the dry solid recrystallized before use. Melting point 98.5°–100.5° C. and the NMR corresponds to the product.

Phosphonylation of chymotrypsin by all three of the foregoing nitrophenyl phenacyl methylphosphonates was much faster than can be measured by conventional methods. The rate at pH 7.8 and 25° C. is estimated to be $>100 M^{-1} s^{-1}$ for NPMN and PMN, and $>10 M^{-1} s^{-1}$ for MPMN. Under the same conditions, the phosphonylation rates of trypsin, thrombin and plasmin by PMN were about $6M^{-1}s^{-1}$, and the rates of phosphonylation by NPMN were faster than $10M^{-1}s^{-1}$.

Inactivation of the enzymes was effected by the introduction of the phosphonate ester from 0.3–0.05M methanolic stock solutions in less than 30% of the total volume of the incubation mixture. Methanol, unlike other common cosolvents, does not cause any denaturation of the enzymes in this concentration. Complete inactivation of the enzymes was verified by two techniques: 1. by spectroscopic monitoring of the release of 4-nitrophenol, and 2. by simultaneous monitoring of declining enzyme activity.

The incubation mixtures were diluted typically to 2.0 ml volume with the appropriate buffer at desired pH's for reactivation. Generally, reactivation rates were least at a pH of about 6 to 7, and maximum at a pH of about 8.5 to 9.5. In all dephosphonylation reactions, simple first order kinetic behavior was observed, indicating the presence of a homogeneous species. Recovering enzyme activity was monitored in each case by drawing aliquotes from the reactivation mixture and titrating for enzyme activity. Active site titrants were 4-methylumbelliferyl-4-trimethylammoniumcinnamate chloride (MUTMAC) for chymotrypsin, 4-methylumbelliferyl 4'-guanidino benzoate (MUGB) for trypsin and thrombin, N-p-tosyl-gly-pro-lys-4-nitroanilide in 0.55 mM aqueous solutions for plasmin and H-D-Ile-Pro-Arg-4-nitroanilide (S-2248) for t-PA. Dephosphonylation rates were studied at 25.0°±0.1° C. with the exception of phenacyl methylphosphonyl chymotrypsin, which was studies at 34.4°±0.2° C.

Figure 2:
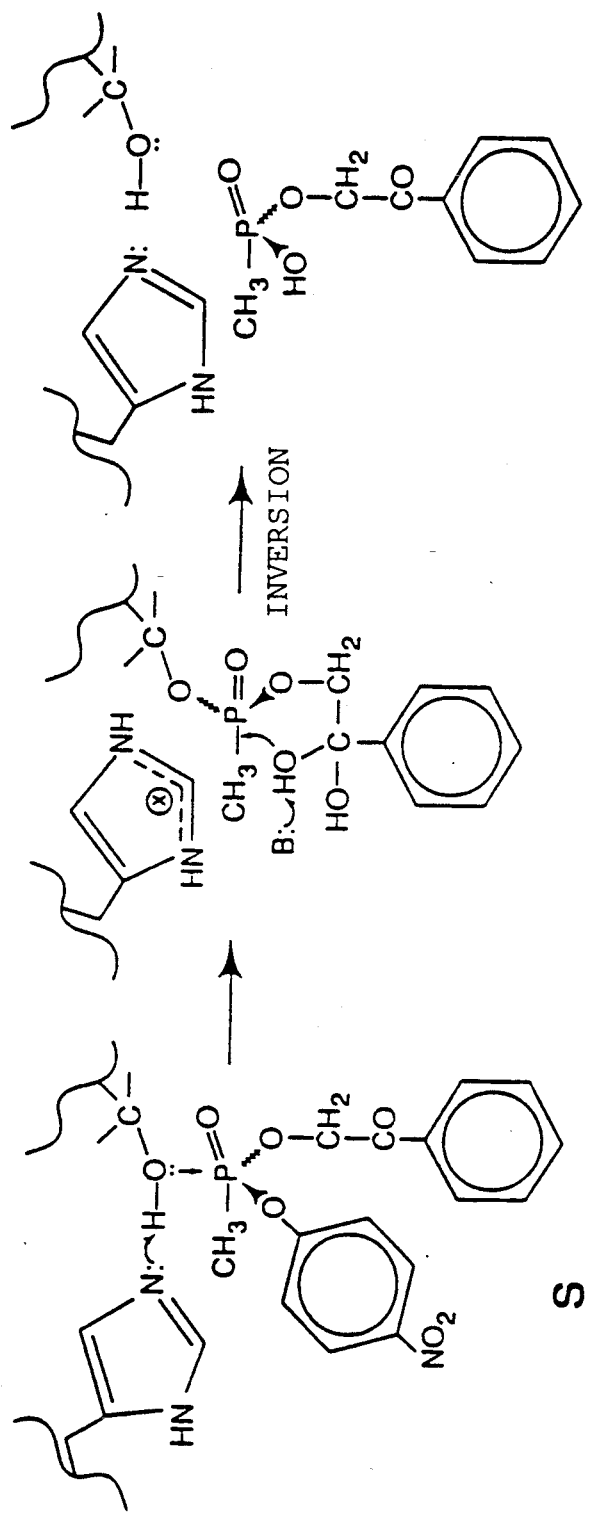
FIG. 2 illustrates the enzymic phosphonylation and dephosphonylation process in accordance with the present invention.

The mechanism of the deactivation/reactivation reactions are illustrated in the reaction equations set forth in the drawings. FIG. 1 depicts the fundamental reaction mechanism for the hydrolytic decomposition of PMN to facilitate an understanding of the present invention. FIG. 2 depicts the mechanism of the present invention. It shows, first, the reaction of a serine hydrolase enzyme with PMN to form the phenacyl methylphosphonyl adduct with the enzyme. That is followed by the intramolecularly catalyzed dephosphonylation to free the enzyme and form phenacyl methylphosphonate. This phosphonylation/dephosphonylation reaction is further illustrated by the following specific examples of the invention.

EXAMPLE 1

Chymotrypsin

Bovine pancreatic α-chymotrypsin (EC 3.4.21.1) was obtained from Sigma Chemical Co. (Sigma Type II 87F-8195) as a salt-free, lyophilized, three-times recrystallized powder with an activity of 52 BTEE units/mg. It was inhibited with an eight fold excess of the racemic mixture of each of PMN and NPMN under which condition the fast isomer should react predominantly. Excess inhibitor was allowed to hydrolyze at pH 8 in 10 minutes.

For generation of a racemic mixture of 4-nitrophenacyl methylphosphonyl-chymotrypsin, the inactivation step was carried out in concentrated solutions of the enzymes (0.5–1 mM) in excess over the inhibitor to assure the generation of an adequate amount of inhibited enzyme even for the slower reacting stereoisomer of the inhibitor. Although the PMN's are subject to fairly rapid intramolecular decomposition at above neutral pHs, their phosphonylation of the serine hydrolases seems to be much more facile. Surprisingly, no sign of biphasic kinetics could be observed, indicating that the slower isomer of NPMN does not react with chymotrypsin to any significant amount at pH 8.0 in 0.05M phosphate buffer.

The timecourse of dephosphonylation of 4-nitro at 25° C. or unsubstituted phenacyl methylphosphonyl-chymotrypsin at 34.4° C., was monitored by drawing aliquots from the solution of the inactivated enzyme and assaying it with the active-site titrant MUTMAC for spectrofluorometric measurements. A reactivation or dephosphonylation half-life time for the PMN inhibited enzyme of 119 minutes was observed, and 10 minutes for the NPMN inhibited enzyme, at pH 7.6 (see Table V).

EXAMPLE 2

Trypsin

Porcine pancreatic trypsin (3.4.21.4) from Sigma Chemical Co. (Sigma Type 56F-0620), a dialyzed, recrystallized, salt-free powder with an activity of 7500 BAEE units/mg, was dissolved in deionized distilled water in 100 mg/ml concentrations and the pH was adjusted to 7.2 with NaOH. The solution was allowed to stand at 25° C. for two hours for autocatalytic destruction of the less stable α form. A fraction of the trypsin stock solution containing about 65 nmoles was then inhibited with 500 nmoles of PMN as well as NPMN contained in 0.02 mL methanolic solutions at 25° C. for 15 minutes. Reactivation was then studied in 0.2M phosphate buffers at pH's ranging from 6.5 to 9.5. The inhibition of trypsin by NPMN was not reproducible, most likely due to the rapid hydrolysis of NPMN in comparison to inhibition of the enzyme.

The timecourse of dephosphonylation of 4-nitro or unsubstituted phenacyl methylphosphonyl-trypsin at 25° C., was monitored by drawing aliquots from the solution of the inactivated enzyme and assaying it with the active-site titrant MUGB for spectrofluorometric measurements. A reactivation or dephosphonylation half-life time for he PMN inhibited enzyme of 85 minutes was observed, at pH 7.6 (see Tables IV and V).

EXAMPLE 3

Thrombin

Human plasma thrombin (EC 3.4.21.5) was obtained from Sigma Chemical Co. (Sigma T-3010) as fine lyophilized powder at 3700 NIH unit/mg. An aliquot of 0.2 pmole thrombin in 0.6 u/uL solution at pH 6.5 was inhibited with 60 nmoles of PMN and incubated for 30 min. at 25° C. Dephosphonylation was studied in 0.1M TRIS buffers at appropriate pH's.

The timecourse of dephosphonylation of phenacyl methylphosphonyl-thrombin at 25° C., was monitored by drawing aliquots from the solution of the inactivated enzyme and assaying it with the active-site titrant MUGB for spectrofluorometric measurements. A reactivation or dephosphonylation half-life time of 39 minutes was observed, at pH 7.6 (see Table V).

EXAMPLE 4

Plasmin

Bovine plasmin (fibrinolysin 3.4.21.7) was also obtained from Sigma Chemical Co. (Sigma P-7911) as a fine lyophilized powder at 7 WHO unit/mg. It was dissolved in 8 mg/mL solution in 0.1M TRIS buffer with 0.2M NaCl at pH 7.4. The stock solution was 200 nM in active sites, based on titration with MUGB. An aliquot of the stock solution containing 10 pmole plasmin was inhibited with 90 nmole PMN and incubated for 15 min at 25° C. The reactivation buffer was 0.1M TRIS.

The timecourse of dephosphonylation of phenacyl methylphosphonyl-plasmin at 25° C., was monitored by drawing aliquots from the solution of the inactivated enzyme and assaying it with an efficient active site titrant of plasmin, N-p-tosyl-gly-pro-lys-4-nitroanilide in 0.55 mM aqueous solutions. Initial rates of 4-nitrophenylaniline release at 400 nm were measured spectrophotometrically to measure returning enzyme activity. A reactivation or dephosphonylation half-life time of 14.4 minutes was observed, at pH 7.6 (see Table V).

EXAMPLE 5 t-PA

Following the procedures of the foregoing examples, similar experiments were performed with tissue-type plasminogen activator enzyme (t-PA), and representative data for its reactivation or dephosphonylation from the covalent adducts of PMN, MOPMN, and MPMN are given in Table VI, below.

The present invention is further exemplified by the kinetic data set forth in Tables I through VI, below. Although the PMN's are subject to fairly rapid intramolecular decomposition (see Table I) at pH's above neutral, their phosphonylation of the serine hydrolases seems to be much more facile with rate constants $>20 M^{-1} s^{-1}$ for NPMN at 25° C. Data from stopped-flow kinetic measurements for trypsin inhibition by the enantiomers of PMN's are in Tables II–III. In all dephosphonylation reactions, simple first order kinetic behavior was observed indicating the presence of a homogeneous species. Rates were the same from adducts unpurified or purified on a Sephadex-25 column. A slight correction term was needed for declining enzyme activity in runs followed for several hours. There was a slight buffer dependence of the rates of reactivation of trypsin from every adduct studied both in phosphate and TRIS; the buffer dependence was studied and extrapolation to zero buffer concentration was performed for all data. Table IV shows a comparison of reactivation rates of trypsin from four of the phenacyl methylphosphonyl adducts of trypsin under similar conditions. First order rate constants at pH 7.6 are also tabulated in Table V for chymotrypsin recovery from its adduct with PMN at 34.4°±0.2° C., for chymotrypsin recovery at 25.0°±0.1° C. from its adduct with NPMN, and for trypsin, thrombin and plasmin recovery at 25.0°±0.1° C. from their adducts with PMN. Table VI summarizes the reactivation data for t-PA adducts with three PMN's.

TABLE I

First-Order Rate Constants for the Hydrolysis of 4-Substituted PNMs in pH 7.75, 0.10M Phosphate Buffer at $\mu = 0.3M$ (KCl) and $25.00 \pm 0.05°$ C.

| compound | $10^3 k_{obs}$, $s^{-1}$ | $t_{\frac{1}{2}}$, min |
|---|---|---|
| PMN | 6.40 ± 0.59 | 2.0 |
| MPMN | 3.17 ± 0.27 | 3.0 |
| MOPMN | 2.18 ± 0.02 | 5.0 |
| NPMN | 145 ± 13 | 0.1 |
| CPMN | 16.8 ± 0.5 | 1.0 |

TABLE II

First-Order Rate Constants for the Inactivation of Trypsin by 4-Substituted-PMNs and the Corresponding Non-Enzymatic Hydrolysis in pH 7.75, 0.10M Phosphate Buffer at $25.0 \pm 0.1°$ C.[a]

| | $10^3 k$, $s^{-1}$ | | |
|---|---|---|---|
| Z | $k_{1obs}$ (n)[b] | $k_{2obs}$ (n)[b] | $k_{hydr}$ (n)[b] |
| H | 292 ± 13 (5)[c] | 6.21 ± 0.12 (3)[d] | 6.40 ± 0.59 (3)[d] |
| CH$_3$ | 113 ± 6 (3)[c] | 3.63 ± 0.02 (3)[d] | 3.17 ± 0.27 (3)[d] |
| OCH$_3$ | 121 ± 4 (12)[c] | 2.43 ± 0.04 (3)[d] | 2.18 ± 0.02 (3)[d] |
| NO$_2$ | 127 ± 5 (12)[c] | 166 ± 9 (4)[d] | 145 ± 13 (4)[d] |
| Cl | 76 ± 4 (19)[c,d] | 13.9 ± 0.7 (4)[d] | 16.8 ± 0.5 (3)[d] |

[a]The concentration of trypsin in the reaction mixture was $3.3 \times 10^{-4}$M, over 40 times in excess of the inhibitor.
[b]number of runs.
[c]data collected by stopped flow method.
[d]data collected by conventional method on L-7 UV-Vis Spectrophotometer.

TABLE III

Second-order Rate Constants for the Inactivation of Trypsin by 4-Substituted PMNs in pH 7.75. 0.10M Phosphate Buffer at $25.0 \pm 0.1°$ C.[a]

| | $K_1$, $M^{-1} s^{-1}$ (n)[b] | enantioselectivity ($k_{1obs}/k_{2obs}$) |
|---|---|---|
| H | 884 ± 39 | >47.0 |
| CH$_3$ | 341 ± 17 | >31.1 |
| OCH$_3$ | 366 ± 14 | >49.8 |
| Cl | 231 ± 12 | >5.0 |

TABLE IV

First Order Rate Constants (min$^{-1}$) for Trypsin Reactivation from its Covalent Adducts Formed with PMNs at $\mu = 0.6M$ (KCl), $25.0 \pm 0.1°$ C.

| compound | buffer | $10^3 K_{obs}$ (n)[a] | $t_{\frac{1}{2}}$, min |
|---|---|---|---|
| PMN | pH 6.97, 0.20M phosphate | 3.25 ± 0.61 (2) | 213 |
| MPMN | pH 6.91, 0.10M phosphate | 33.7 ± 1.8 (3) | 20.6 |
| MOPMN | pH 6.97, 0.06M TRIS | 5.55 ± 0.38 (1) | 125 |
| CPMN | pH 7.00, 0.12M TRIS | 97.5 ± 17.2 (1) | 7.1 |

[a]number of runs

TABLE V

First Order Rate Constants (min$^{-1}$) for the Reactivation of Serine Protease Enzymes from their Adducts formed with PMNs at pH 7.6 and 25.0° C.

| enzyme | inhibitor | $10^3 k_{obs}$ (n = 3) | $t_{\frac{1}{2}}$, min |
|---|---|---|---|
| chymotrypsin[a] | PMN | 5.8 | 119 |
| chymotrypsin | NPMN | 71 | 10 |
| trypsin | PMN | 8.2 | 85 |
| thrombin | PMN | 18 | 39 |
| plasmin | PMN | 48 | 14.4 |

[a]34.4 °C.

TABLE VI

First-Order Rate Constants (min$^{-1}$) for the reactivation of t-PA from its Adducts with PMNs at $25.0 \pm 0.1°$ C.

| compound | reactivation buffer | $k_{obs}$ | $t_{\frac{1}{2}}$, min |
|---|---|---|---|
| *Single-Chain t-PA* | | | |
| PMN | pH 7.50, 0.36M Tris-HCl[a] | 0.004 ± 0.003[d] | 173 |
|  |  | 0.002 ± 0.001[d] | 346 |
|  | pH 8.23, 0.06M Tris-HCl[b] | 0.023 ± 0.047[d] | 30 |
|  | pH 8.23, 0.06M Tris-HCl[a] | 0.019 ± 0.030[d] | 36 |
| MOPMN | pH 7.50, 0.36M Tris-HCl[a] | 0.057 ± 0.068[d] | 12 |
|  | pH 8.23, 0.06M Tris-HCl[b] | 0.035 ± 0.036[d] | 20 |
|  |  | 0.050 ± 0.053[c] | 14 |
| MPMN | pH 8.23, 0.06M Tris-HCl[b] | 0.029 ± 0.031[c] | 24 |
| *Two-Chain t-PA* | | | |
| PMN | pH 8.23, 0.06M Tris-HCl[c] | 0.026 ± 0.017[c] | 27 |
| MOPMN | pH 8.23, 0.06M Tris-HCl[c] | 0.028 ± 0.002[c] | 25 |
| MPMN | pH 8.23, 0.06M Tris-HCl[c] | 0.042 ± 0.016[c] | 16 |

[a]No BSA and triton X-100 in either reactivation buffer or assay buffer.
[b]0.5 mg/ml BSA and 0.1 g/L Triton X-100 in both reactivation buffer and assay buffer.
[c]Same as in [b], except that the concentration of BSA is 1 mg/mL.
[d]The final concentration of S-2288 for activity assay is 0.83 mM.
[e]The final concentration of S-2288 for activity assay is 0.50 mM.

Applicant has further found that water, phosphate dianion, TRIS and hydroxide ion all catalyze the hydrolysis of the PMN esters. The data is completely consistent with the intramolecular displacement of 4-nitrophenol which applicant has observed by: 1. stoichiometric release of 4-nitrophenol, and 2. several hundred fold faster hydrolysis than alkoxy or benzyl substituted phosphonate analogues of the phenacyl group. Applicant suggests an, at least partially, rate determining proton transfer step in the cyclization step with solvent isotope effects over 2 at pH's 7.45 and 9.25, where the hydrate is expected to exist in the protonated form (FIG. 1). The reaction becomes too rapid at pH 10 for observation. A plateau might be expected at pH's above 10, when the hydrate is fully ionized (pK about 11-13). The log rate - pH profile, however, indicates a slope of near one and is again consistent with partial rate limiting proton removal from the carbonyl hydrate. The ionic strength dependence is consistent with a greater charge delocalization at the transition state than in the ground state in which the base catalyst is fully ionized.

It is shown above that phenacyl and substituted phenacyl 4-nitrophenyl methylphosphonate derivatives temporarily inactivate chymotrypsin, trypsin, thrombin, plasmin and tissue-type plasminogen activator enzymes fully and very effectively. Electronic effects of the para substituents on the phenacyl group certainly have an effect on inactivation. Chymotrypsin was inactivated more readily than the trypsin-like enzymes indicating a greater complementarity of the aromatic side groups of PMN with the chymotrypsin specificity requirement. Trypsin was studied extensively with all five PMN derivatives and showed enantioselectivity over 30 fold toward the phosphonate esters (see Tables II and III). These reactions took place as predicted. Trypsin-like enzymes recovered faster from the phenacyl methylphosphonyl adduct than chymotrypsin; plasmin and tissue-type plasminogen activator enzyme recovering the fastest. That specific enzyme-inhibitor interactions govern residence times on the enzymes was further evidenced by slower dephosphonylation rates for some of the more reactive inhibitors that provide stronger interactions with the specificity pocket (Table V). Thus the enzymes participate in regeneration of their activity at a characteristic rate of their own, possibly by facilitating proton removal from the carbonyl hydrate for intramolecular nucleophilic attack (FIG. 2).

Although the dephosphonylation rates for the above-described adducts are pH dependent, the reactions are effective over the physiological pH range and pH dependence is small in all cases. This suggests that it is not hydroxide ion that is responsible for catalysis in this reaction. A slight dependence on phosphate dianion is observed with chymotrypsin and trypsin reactivation from the PMN adduct. The dependence of trypsin recovery from its adducts was studied for a wide range of pH values and could be fit to a sigmoidal function:

$$k_{obs} = \frac{k^{lim} K_a}{K_a + [H]} + k_{HOH}$$

An upper limit of 0.0142±0.001 min$^{-1}$ for the phenacyl derivative and 0.0151±0.001 min$^{-1}$ for the 4-methoxyphenacyl derivative give the maximal rate of recovery at pH's above 7.6. This recovery rate is dependent on an ionizing group with an apparent pK of 8.0±0.2 for the former and 7.92±0.3 for the latter, most likely, on the enzyme. The identity of this group is uncertain, but could well be the active site His which has a pK$_a$ slightly lower than what is observed here. It may, however, be difficult for the His to get into the proximity of the hydrated keto group which probably binds near the specificity pocket of trypsin. Molecular modeling of the adduct can illuminate the question. The lower limit to the reactivation rate can represent the rate for the water-catalyzed reaction (K$_{HOH}$), i.e., the reaction path in which water removes the proton from the carbonyl hydrate. Similar characterization of the pH dependence was done for chymotrypsin adducts with PMN and NPMN, thrombin adducts with PMN, plasmin adducts with PMN, and t-PA adducts with PMN, MPMN and MOPMN.

The broad range of rates of serine protease reactivation and the small pH dependence are both consistent with self-catalyzed enzyme reactivation from the phenacyl methylphosphonyl adducts with varying efficiency. The small solvent isotope effects 1.2-1.3, contrary to what is observed for the non-enzymic hydrolysis, also support a mechanism in which rapid proton removal from the carbonyl hydrate of the phenacyl group by the unprotonated His (or other residue) at the active site might be followed by a rate-determining intramolecular attack of the anion of the carbonyl hydrate on the central phosphorus atom to form the oxyphosphorane and expel the enzyme.

The very efficient recovery of the serine proteases from adducts formed with the present group of phosphonate esters is unprecented with other known phosphonate ester inhibitors of serine proteases. This reversible inhibition may be attributed to the unique propensity of the phenacyl group to assist in an intramolecular displacement of the active site Ser from the covalent adduct. The enzymes, however, actively participate in their reactivation by providing general base assistance of proton removal from the carbonyl hydrate. If His is indeed the base catalyst, it is less available at physiological pH than in the native enzyme because of its higher pK.

The foregoing detailed description is given by way of example to facilitate an understanding of the invention. Numerous variations and modifications will become apparent to those skilled in the art. Such variations and modifications as are embraced by the spirit and scope of the appended claims are contemplated as being within the purview of the invention.

I claim:

1. An adduct of a serine hydrolase with a phosphonate or phosphate represented by the formula

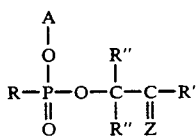

wherein R is an alkyl or alkoxy radical, A is a phenyl or a naphthyl radical, R' is a phenyl or alkyl radical, R" is hydrogen or methyl, and Z is an electronegative group, wherein the adduct deactivates the serine hydrolase and is dephosphonylated by intramolecular catalysis to reactivate the serine hydrolase.

2. The adduct of claim 1, wherein R is a lower alkyl radical and Z is oxygen, nitrogen or sulfur or a monovalent hydroxy or amino group.

3. The adduct of claim 2, wherein A is a phenyl radical, and Z is oxygen, nitrogen or sulfur.

4. The adduct of claim 3, wherein A is a para substituted phenylene.

5. The adduct of claim 3 wherein A is a substituted phenylene selected from nitro, chloro, methoxy, methyl or amino phenylene.

6. The adduct of claim 5, wherein the substituted phenylene is substituted in the para position.

7. A method for temporarily inhibiting or deactivating a serine hydrolase by reversibly phosphonylating said serine hydrolase with a phosphonate represented by the formula

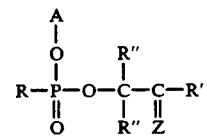

wherein R is an alkyl radical, A is a phenyl or a naphthyl radical, R' is a phenyl or alkyl radical, R" is hydrogen or methyl, and Z is an electronegative group, and wherein dephosphonylation to reactivate the serine hydrolase is intramolecularly catalyzed.

8. The method as set forth in claim 7, wherein R is a lower alkyl radical and Z is oxygen, nitrogen or sulfur or a monovalent hydroxy or amino group.

9. The method as set forth in claim 8, wherein A is a phenyl radical, and Z is oxygen, nitrogen or sulfur.

10. The method as set forth in claim 9, wherein A is a para substituted phenylene.

11. The method as set forth in claim 9, wherein A is a substituted phenylene selected from nitro, chloro, methoxy, methyl, or amino phenylene.

12. The method as set forth in claim 11, wherein the substituted phenylene is substituted in the para position.

13. The adduct of claim 1, wherein the serine hydrolase is an acetylcholinesterase, chymotrypsin, mast cell chymase, cathepsin G, trypsin, thrombin, plasmin, tissue plasminogen activator, phospholipase and serine protease.

14. The adduct of claim 1, wherein the phosphate or phosphate is a phenyl acyl phosphonate.

* * * * *